(12) United States Patent
Diorio et al.

(10) Patent No.: US 10,166,187 B2
(45) Date of Patent: Jan. 1, 2019

(54) CURCUMIN SOLID LIPID PARTICLES AND METHODS FOR THEIR PREPARATION AND USE

(71) Applicant: Capsugel Belgium NV, Bornem (BE)

(72) Inventors: Christopher Diorio, Campbell Hall, NY (US); John Lokhnauth, Fair Lawn, NJ (US)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 15/786,851

(22) Filed: Oct. 18, 2017

(65) Prior Publication Data

US 2018/0036248 A1 Feb. 8, 2018

Related U.S. Application Data

(63) Continuation of application No. 14/771,117, filed as application No. PCT/IB2014/000463 on Mar. 4, 2014.

(60) Provisional application No. 61/773,635, filed on Mar. 6, 2013.

(51) Int. Cl.
*A61K 9/16* (2006.01)
*A61K 31/12* (2006.01)
*A61K 9/50* (2006.01)
*A61K 36/9066* (2006.01)

(52) U.S. Cl.
CPC .......... *A61K 9/1694* (2013.01); *A61K 9/1617* (2013.01); *A61K 9/1623* (2013.01); *A61K 9/5063* (2013.01); *A61K 31/12* (2013.01); *A61K 36/9066* (2013.01)

(58) Field of Classification Search
CPC .................................................... A61K 9/1694
See application file for complete search history.

(56) References Cited

U.S. PATENT DOCUMENTS

| 5,635,200 | A | 6/1997 | Douglas et al. |
|---|---|---|---|
| 6,572,892 | B1 | 6/2003 | Ioulalen et al. |
| 7,235,260 | B2 | 6/2007 | Crew et al. |
| 7,625,507 | B2 | 12/2009 | Ray et al. |
| 7,887,844 | B2 | 2/2011 | Appel et al. |
| 2004/0265375 | A1 | 12/2004 | Platteeuw et al. |
| 2005/0123615 | A1 | 6/2005 | Ray et al. |
| 2008/0200452 | A1 | 8/2008 | Obermeier et al. |
| 2009/0131373 | A1 | 5/2009 | Gopro et al. |
| 2009/0324703 | A1 | 12/2009 | Frautschy et al. |
| 2010/0221298 | A1 | 9/2010 | Ioualalen |
| 2016/0000714 | A1 | 1/2016 | Diorio et al. |
| 2017/0112762 | A1 | 4/2017 | Sivert et al. |

FOREIGN PATENT DOCUMENTS

| EP | 1030687 | 8/2000 |
|---|---|---|
| EP | 1691787 | 8/2006 |
| EP | 1827382 | 9/2007 |
| EP | 2044929 | 4/2009 |
| EP | 2964243 | 1/2016 |
| WO | WO99/65448 | 12/1999 |
| WO | WO2004/084856 | 10/2004 |
| WO | WO2004/084865 | 10/2004 |
| WO | WO2005/053654 | 6/2005 |
| WO | WO2006/070141 | 7/2006 |
| WO | WO2007/101551 | 9/2007 |
| WO | WO2012/023142 | 2/2012 |
| WO | WO2014/135967 | 9/2014 |
| WO | WO2015/189726 | 12/2015 |
| WO | WO2016/087261 | 6/2016 |

OTHER PUBLICATIONS

Anand et al., "Bioavailability of Curcumin: Problems and Promises," *Molecular Pharmaceutics*, 4(6):807-818 (Nov.-Dec. 2007).
Cuomo et al., "Comparative Absorption of a Standardized Curcuminoid Mixture and Its Lecithin Formulation," *Journal of Natural Products*, 74(4):664-669 (Apr. 2011).
Dadhaniya, P. et al., "Safety assessment of a solid lipid curcumin particle preparation: Acute and subchronic toxicity studies," *Food and Chemical Toxicology*, vol. 49, No. 8, pp. 1834-1842 (May 2011).
Final Office Action from the United States Patent and Trademark Office for U.S. Appl. No. 14/771,117, dated May 19, 2017.
Comes, G. V. L. et al., "Characterization and Shelf Life of β-Carotene Loaded Solid Lipid Microparticles Produced With Stearic Acid and Sunflower Oil," *Braz. Arch. Biol. Technol.*, 56(4):663-671 (Jul./Aug. 2013).
International Preliminary Report on Patentability for PCT/IB2014/000463 (dated Sep. 17, 2015).
International Preliminary Report on Patentability for PCT/IB2015/053568 (dated Dec. 22, 2016).
International Preliminary Report on Patentability for PCT/EP2015/077428 (dated Jun. 15, 2017).
International Search Report and Written Opinion for PCT/IB2014/000463 (dated Jun. 18, 2014).
International Search Report and Written Opinion for PCT/IB2015/053568 (dated Sep. 14, 2015).
International Search Report and Written Opinion for PCT/EP2015/077428 (dated Jan. 29, 2016).
Kakkar et al., "Exploring solid lipid nanoparticles to enhance the oral bioavailability of curcumin," *Mol. Nutr. Food Res.*, 55(3):495-503 (Mar. 2011).
Office Action from the European Office Action for European Patent Application No. 14717186.2, dated Sep. 18, 2017.
Office Action from the United States Patent and Trademark Office for U.S. Appl. No. 14/771,117, dated Sep. 23, 2016.

(Continued)

*Primary Examiner* — Gina C Justice (74) *Attorney, Agent, or Firm* — Klarquist Sparkman, LLP (57) ABSTRACT

Solid lipid particles comprising a lipid hydrophobic matrix and from about 5 wt. % to about 30 wt. % of curcumin, and methods of making and treatment thereof.

13 Claims, 3 Drawing Sheets

(56) References Cited

OTHER PUBLICATIONS

Office Action from the United States Patent and Trademark Office for U.S. Appl. No. 15/313,512, dated May 19, 2017.
Marcyzlo et al., "Comparison of systemic availability of curcumin with that of curcumin formulated with phosphatidylcholine," *Cancer Chemother. Pharmacol.*, 60(2):171-177 (Jul. 2007).
Passerini, N. et al., "Solid lipid microparticles produced by spray congealing: Influence of the atomizer on microparticle characteristics and mathematical modeling of the drug release," *Journal of Pharmaceutical Sciences*, 99(2):916-931 (Feb. 2010).
Pawar et al., "Novel lipid based oral formulation of curcumin: Development and optimization by design of experiments approach," *International Journal of Pharmaceutics*, 436(1-2):617-623 (Jul. 2012).
Restriction Requirement Action from the United States Patent and Trademark Office for U.S. Appl. No. 14/771,117, dated May 6, 2016.
Solanki, K., Incorporation of Curcumin in Lipid Based Delivery Systems and Assessment of its Bioaccessibility, Thesis submitted to the Graduate School-New Brunswick Rutgers, The State University of New Jersey, 91 pages (Oct. 2012).

CURCUMIN SOLID LIPID PARTICLES AND METHODS FOR THEIR PREPARATION AND USE

CROSS REFERENCE TO RELATED APPLICATIONS

This application is a continuation of U.S. patent application Ser. No. 14/771,117, filed Aug. 27, 2015, which is the U.S. National Stage of International Application No. PCT/IB2014/000463, filed Mar. 4, 2014, which was published in English under PCT Article 21(2), which in turn claims the benefit of U.S. Provisional Application No. 61/773,635, filed Mar. 6, 2013. These applications are incorporated herein in their entirety.

DESCRIPTION

Curcum in (IUPAC name 1,7-bis(4-hydroxy-3-methoxyphenyl)-1E,6E-heptadiene-3,5-dione) is a polyphenolic compound derived from the herbal remedy and dietary spice, turmeric. Among the various beneficial pharmacologic properties curcumin has been known to possess are antioxidant, antimicrobial, anticarcinogenic, and anti-inflammatory properties. The compound has been involved in induction of cell arrest and apoptosis, inhibition of tumor invasion and angiogenesis, and suppression of cyclooxygenase 2 (COX-2) expression. Curcumin has also been recognized as a neuro-, cardio-, and hepato-protective agent. Preclinical studies of curcumin indicate therapeutic potential of the compound in treating a variety of diseases including cancer, stroke, Alzheimer's disease, irritable bowel syndrome (IBS), atherosclerosis, arthritis, and aging, among others.

Figure 1:
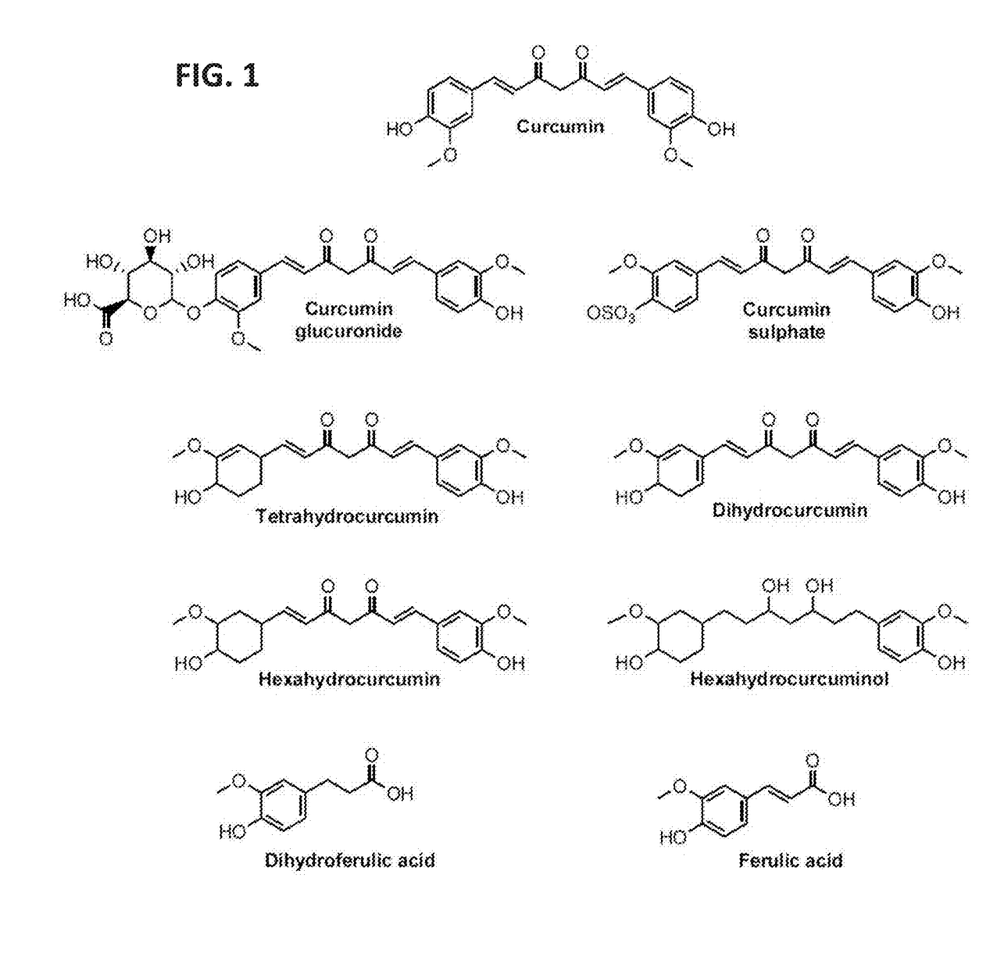
FIG. 1 illustrates chemical structures of curcumin and metabolites thereof.

Despite these beneficial pharmacologic properties, curcumin's low bioavailability has proved an impediment to its use. In particular, as discussed in Anand et al., "Bioavailability of Curcumin: Problems and Promises," *Molecular Pharmaceutics* vol. 4, no. 6, pp. 807-18 (2007), curcumin suffers from low intrinsic activity and poor absorption. The chemical structures of curcumin and its downstream metabolic products are shown in FIG. 1. These metabolic products do not display the beneficial pharmacologic properties of curcumin itself. Thus, curcumin's high rate of metabolism by mammalian organisms results in rapid elimination of the compound and termination of its desirable pharmacologic effects.

Various attempts have been made to improve the bioavailability of curcumin. Anand et al. discloses that concurrent administration of curcumin with piperine, a glucuronidation inhibitor, to rats and humans have shown to increase in vivo curcumin bioavailability. Other studies have used pretreatment with eugenol or terpeneol to improve skin absorption of curcumin. Anand et al. also discloses that complexes of curcumin with phospholipids, in particular, phosphatidylcholine, has shown a five-fold increase in peak plasma levels of curcumin in rats. Complexes of curcumin with phosphatidylcholine are available as a commercial product trademarked as MERIVA®. Anand et al., further disclose that liposomes, micelles, and solid lipid nanoparticles (SLNs) have been investigated as drug delivery platforms for curcumin.

Kakkar et al., "Exploring solid lipid nanoparticles to enhance the oral bioavailability of curcumin," *Mol. Nutr. Food Res.* vol. 55, pp. 495-503 (2011) discloses in vivo studies using oral administration of curcumin-loaded SLNs to rats. At dosages of 50, 25, 12.5 and 1 mg/kg, Kakkar et al. reports increased bioavailability at factors of 39, 32, 59, and 155, relative to a control of solubilized curcumin at the same dose.

Other documents addressing curcumin bioavailability include: Pawar et al., "Novel lipid based oral formulation of curcumin: Development and optimization by design of experiments approach," *International Journal of Pharmaceutics* vol. 436, pp. 617-23 (2012); Cuomo et al., "Comparative Absorption of a Standardized Curcuminoid Mixture and Its Lecithin Formulation," *Journal of Natural Products* vol. 74, pp. 664-69 (2011); Marcyzlo et al., "Comparison of systemic availability of curcumin with that of curcumin formulated with phosphatidylcholine," *Cancer Chemother. Pharmacol.* vol. 60, pp. 171-77 (2007): US 2009/0324703 A1; US 2009/0131373 A1; WO 2007/101551 A2; and WO 2012/023142 A2.

The present disclosure generally relates to a solid lipid particles comprising curcumin. As used herein, the terms "galenic system," "lipidic particle," "lipid particle," "droplet," and "lipidic droplet" should be understood to have substantially the same meaning. In one embodiment, solid lipid particles comprising curcumin in accordance with the present disclosure enable increased bioavailability of curcumin. Solid lipid particles according to the disclosure also provide one or more of masking of taste, masking of odor, stabilization of the active curcumin constituent, modulation of the release profile of curcumin, ease of handling, predictability of dosing, and minimization of any mucosal irritation, toxicity, and/or gastro-toxicity. In some embodiments, solid lipid particles comprising curcumin in accordance with the present disclosure are capable of delayed release of curcumin, particularly so that curcumin is not released into the stomach during ingestion. Thus, in a further preferred embodiment, the solid lipid particles comprising curcumin are resistant to acidic pH.

It is to be understood that both the foregoing general description and the following detailed description are exemplary and explanatory only and are not restrictive of the claimed subject matter.

DETAILED DESCRIPTION

As used herein, reference to an element by the indefinite article "a" or "an" does not exclude the possibility that more than one of the element is present, unless the context clearly requires that there is one and only one of the elements. The indefinite article "a" or "an" thus usually means "at least one." The disclosure of numerical ranges should be understood as referring to each discrete point within the range, inclusive of endpoints, unless otherwise noted. The term "about" as used in the disclosure of numerical ranges indicates that deviation from the stated value is acceptable to the extent that the deviation is the result of measurement variability and/or yields a product of the same or similar properties.

Curcumin may be found in several tautomeric forms, e.g. a 1,3-diketo and enol forms. Commercial forms of curcumin may often comprise one or more curcuminoid compounds, such as (besides curcumin itself), desmethoxycurcumin and bisdesmethoxycurcumin and cumerone oils. An exemplary embodiment of a commercial form of curcumin comprises from about 75% by weight to about 80% by weight of curcumin, from about 15% by weight to 20% by weight of desmethoxycurcumin, and from about 1% by weight to about 15% by weight of bisdesmethoxycurcumin. A commercial form of curcumin may comprise, for example, about 77% by weight of curcumin, about 17% by weight of demesthoxycurcumin, and about 6% by weight of bisdesmethoxycurcumin. The chemical structures of several forms of curcumin and/or curcuminoid compounds is shown below:

Curcumin

Desmethoxycurcumin

Bisdesmethoxycurcumin

As used herein, "curcumin" and/or "curcurninoid compounds" is understood to refer to tautomeric, commercial, or otherwise chemically equivalent forms of curcumin that substantially retain the pharmacologic properties of curcumin as discussed (e.g. antioxidant, antimicrobial, anticarcinogenic, anti-inflammatory, etc.), and may include any or all of the curcumin and/or curcuminoid compounds separately or in a mixture.

In one embodiment, solid lipid particles in accordance with the present disclosure comprise a lipid and/or hydrophobic matrix (which may be referred to as a "lipid hydrophobic matrix"). In certain embodiments, the lipid and/or hydrophobic matrix is non-ionizable such that it is not capable of being ionized at physiological pH, where physiological pH is approximately pH 5 to pH 7, more particularly about pH 7.4. Thus in one embodiment, the lipid and/or hydrophobic matrix does not include any acid or basic functions, such as organic or mineral bases. In another embodiment, the solid lipid particles optionally comprise surfactant, surfactant compounds, and/or surface-active agents.

In certain embodiments, the solid lipid particles according to the disclosure comprise surfactant, surfactant compounds and or surface active agents. In certain embodiments, the solid lipid particles in accordance with the disclosure do not contain any organic solvents.

Certain embodiments of solid lipid particles in accordance with the disclosure do not contain any fatty acids. The lipid hydrophobic matrix may also have an end melting point ranging from about 15° C. to about 85° C., e.g. from about 15° C. to about 75° C., or from about 30° C. to about 45° C., or about 37.5° C. In certain embodiments, the lipid hydrophobic matrix optionally include surfactant, surfactant compounds, and/or surface-active agents.

In one embodiment, the lipid hydrophobic matrix comprises natural and/or synthetic oils and/or waxes including glycerides (e.g. monoglycerides, diglycerides, triglycerides, etc. with saturated or unsaturated chains having carbon numbers from $C_6$ to $C_{40}$, e.g. $C_{18}$ to $C_{24}$, $C_8$ to $C_{32}$, $C_{10}$ to $C_{24}$, $C_{18}$ to $C_{18}$, $C_{12}$ to $C_{93}$, etc.), hemisynthetic glycerides or glyceride derivatives with saturated or unsaturated medium to long chain lengths, palm oil, Carnauba wax, Candellila wax, Alfa wax, cocoa butter, ozokerite, vegetable waxes, rice wax, hydrogenated jojoba wax or florali absolute waxes, beeswaxes and modified beeswaxes, fatty alcohols, esters of fatty acids and of alcohols with high molecular weight, sterols such as cholesterol and its esters, vegetable oils such as olive oil, groundnut oil, oils of hydrophobic silicones, cyclomethicones, petroleum waxes or jellies, paraffin oil, paraffin, linear alkanes, and/or mixtures thereof.

It is also possible to use fatty alcohols with high molecular weight (e.g., cetanol, myristoyl alcohol, stearoyl alcohol), esters of acids and alcohols with high molecular weight, for example, esters of linear and saturated acids with even carbon numbers from $C_{14}$ to $C_{20}$, and linear and saturated alcohols with even carbon numbers from $C_{14}$ to $C_{32}$. Esters of fatty acids with carbon numbers from $C_6$ to $C_{12}$ with glycols, e.g. ethylene glycol, propylene glycol, may also be used. The lipid hydrophobic matrix may also comprise an oil or a mixture chosen from oils of hydrophobic silicones with a viscosity of from about 5 centistokes to about 9000 centistokes, cyclomethicones, lipophilic organic fluorinated oils, and/or perhydrosqualene. Oily compounds may be used, such as oleic alcohol, lanoline, sunflower oil, palm oil, olive oil, and oils that are immiscible with water and have a melting point ranging from about 15° C. to about 85° C. The lipid hydrophobic matrix may comprise from about 0.5 weight percent to about 99 weight percent of wax, e.g. from about 1 weight percent to about 50 weight percent of wax.

In preferred embodiments, the lipid hydrophobic matrix comprises waxes which are non-ionizable at physiologic pH, approximately. The lipid hydrophobic matrix advantageously may be "strictly hydrophobic" insofar as it does not contain any detectable traces of water.

In certain embodiments, the lipid hydrophobic matrix comprises a wax, such as those mentioned above, and a non-neutralized fatty acid. The non-neutralized fatty acid may be chosen from fatty acids with linear chains with carbon numbers ranging from $C_4$ to $C_{18}$, for example such as myristic acid, lauric acid, palmitic acid, or oleic acid.

The lipid hydrophobic matrix may also include, for the purposes of adjusting consistency, clays or their oily dispersions, gums of phenylated silicones, starches, and/or fat structuring agents. The lipid hydrophobic matrix may also include a certain number of compounds such as mineral fillers, to modulate its density and plasticity. The mineral fillers may be, for example, talc and/or kaolin. In certain embodiments, mineral fillers are not used.

In one embodiment, the solid lipid particles comprise at least one component chosen from lecithin, COMPRITOL® E. CAPRYOL® 90, GELUCIRE® 43/01, LABRAFAC® or combinations therefore. For example, in a preferred embodiment, a composition of one embodiment comprises about 5 wt. % to about 30 wt. % lecithin, preferably 10 to 15 wt %, and more preferably about 15%; about 5 wt. % to about 15 wt. % COMPRITOL® E, preferably about 5 wt %; and at least about 40 wt. % GELUCIRE® 43/01, preferably about 50 wt. % or about 65 wt %. In another embodiment, a composition comprises about 5 wt. % to about 30 wt. % CAPRYOL® 90, preferably about 20 wt %; 5 wt. % to about 30 wt % LABRAFAC® preferably about 10 wt %; about 5 wt. % to about 15 wt. % COMPRITOL® E, preferably 5 wt %; and at least about 40 wt. % GELUCIRE® 43/01, preferably about 50 wt. % or about 65 wt %. In a preferred embodiment, each of these compositions would further comprise about 15 wt. % curcumin.

Processes for preparation of solid lipid particles are well known to those skilled in the art, and is described in publications WO 1999/65448, WO 2004/084856, and WO 2006/0701417, the disclosures of which are incorporated herein by reference.

In one embodiment, the solid lipid particles in accordance with the present disclosure are obtained by mixing a lipid phase under moderate heat. For example, wax and oil may be mixed at a temperature corresponding to the melting point of the wax, until the mixture obtained has a melting point lower than the melting point of the wax. The initial ratio of the wax to the oil can be modulated so that the melting point of the end mixture is lower than the degradation temperature of the most heat-sensitive component to be incorporated. In one embodiment, the end mixture is a solid at the temperature of its utilization. For example, the end mixture may have a melting point of about 37.5° C. The end mixture is cooled while stirring to a temperature slightly above its melting point, e.g. about 2° C. or about 3° C. above its melting point. One or more active pharmaceutical ingredients may then be added. In accordance with the present disclosure, at least one of the active pharmaceutical ingredients comprise curcumin.

Figure 2:
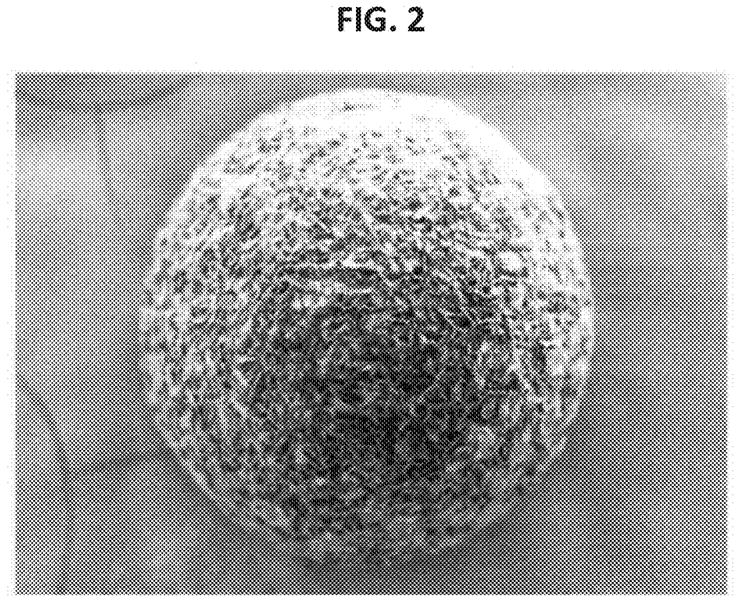
FIG. 2 is a micrograph of a solid lipid particle having a size (average particle diameter) of approximately 250 μm in accordance with the present disclosure.
Figure 3:
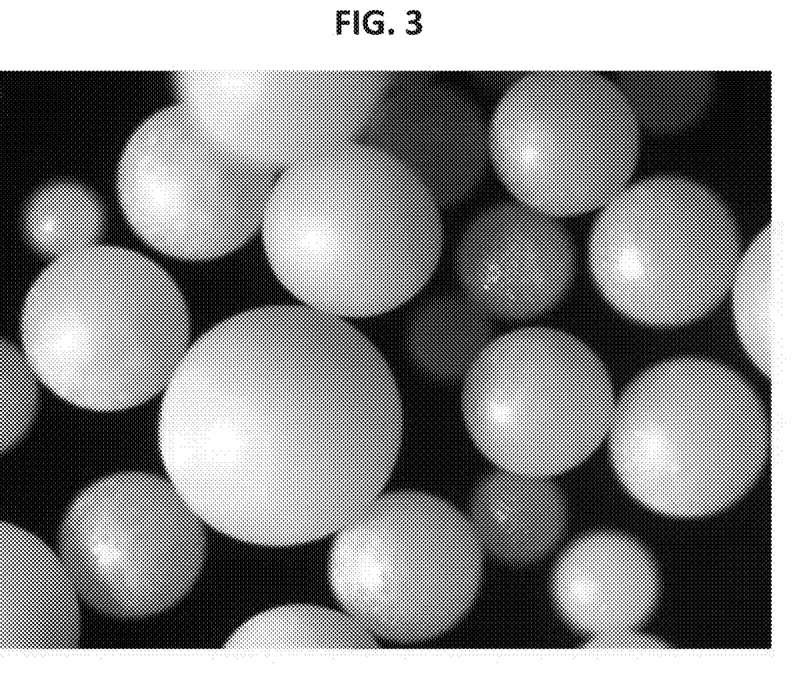
FIG. 3 is a micrograph of solid lipid particles comprising curcumin, in accordance with the present disclosure. The mean particle size of the solid lipid particles is approximately 400 μm.

In a preferred embodiment, addition of the active pharmaceutical ingredient to the mixture is accomplished such that the ingredient is dispersed throughout such means include the use of a homogenizer, disperser, or the use of mechanical agitation or stirring. Sonicators or static mixers may be also be used. Other ingredients may be similarly incorporated at the same or different times. In certain preferred embodiments, the active pharmaceutical ingredient, comprising e.g. curcumin and/or other ingredients, may be subjected to a homogenizing step to form nanoparticles of the active pharmaceutical ingredient, prior to its addition to the mixture. In some embodiments, the active pharmaceutical ingredient may be subjected to a homogenizing step to form nanoparticles of the pharmaceutical ingredient. The homogenizing step may occur before or after addition of the active pharmaceutical ingredient to the mixture. The mixture is then shaped to give solid lipid particles. In certain embodiments, the solid lipid particles have substantially spherical shape as shown in FIG. 2 and FIG. 3.

In a preferred embodiment, shaping is carried out using a gel. The gel may be prepared with a gel-form ing/gelifying, shear-thinning, non-surface-active agent or substance, with which the mixture is not miscible. The mixture may be injected into the gel, for example, through an orifice located at the base of a reaction vessel holding the gel, to form a dispersion. Stirring may be continued throughout injection using a blade equipped with an anchor designed to disperse the mixture and a second axial blade equipped with a three-vaned impeller designed to obtain a dispersion having a desired droplet size or a dispersion having a discontinuous phase of a desired characteristic size. The temperature of the gel may be adjusted to be the same as the temperature of the mixture prior to injection. The concentration of the gelifying agent may range, for example, from about 0.1 g/l to about 30 g/l, e.g. from about 0.2 g/l to about 20 g/l, or sufficiently high to fix the dispersion. The dispersion may then be cooled below the melting point of the mixture. Solid lipid particles may then be separated from the gel, after which, the solid lipid particles may be washed. The particles may be washed with a mixture of water and ethanol, e.g, a mixture comprising water and up to 25 weight percent of ethanol.

Examples of gelifying agents include carboxyvinyl polymers such as polyacrylic polymers not modified by hydrophobic groups or surfactant groups. Other gelifying agents include carrageenans, thickeners and polysaccharidic gels such as xanthenes, guar and carob gels, alginates, cellulose derivatives, pectins, agar, etc. or mixtures thereof.

In certain preferred embodiments, the solid lipid particles in accordance with the present disclosure have particle sizes ranging from about 0.5 μm to about 1500 μm, particularly from about 100 μm to about 1500 μm, and comprise curcumin dispersed in a lipid hydrophobic matrix. The solid lipid particles may further comprise essential oils, flavorings, pigments, fillers, coloring agents, enzymes and coenzymes, preservatives, and other active substances or active components. In one embodiment, the filling or loading ratio of the solid lipid particles ranges from about 0.2 weight percent to about 75 weight percent, relative to the total weight of the solid lipid particles. In a preferred embodiment, the filling or loading ratio of curcumin in the solid lipid particles ranges from about 0.5 weight percent to about 30 weight percent, e.g. from about 5 weight percent to about 30 weight percent, from about 10 weight percent to about 20 weight percent, from about 12 weight percent to about 18 weight percent, relative to the total weight of the solid lipid particles. In certain embodiments; the solid lipid particles comprise about 15 weight percent of curcumin. For oral administration; the solid lipid particles may have a size (average particle diameter) ranging from about 100 μm to about 400 μm. In a preferred embodiment, solid lipid particles in accordance with the present disclosure comprise curcumin having an average particle size diameter ranging from about 100 μm to about 600 μm.

Solid lipid particles in accordance with the present disclosure may comprise at least one additional active component, referring to a therapeutic substance or mixture able to be advantageously administered to humans or animals to diagnose, care for, reduce, treat, or prevent disease—or improve health. As used herein, "active substance," "active component," "active agent," and "active ingredient" have substantially the same meaning. Non-limiting examples of the additional active component include vitamins or provitamins A, B, C, D, E, PP and their esters, carotenoids, anti-radical substances, hydroxyacids, antiseptics, molecules acting on pigmentation or inflammation, biological extracts, antioxidants, cells and cell organelles, antibiotics, macrolides, antifungals, itraconazole, ketoconazole, antiparasitics, antimalarials, adsorbents, hormones and derivatives thereof, nicotine, antihistamines, steroid and non-steroid anti-inflammatories, ibuprofen, naproxen, cortisone and derivatives thereof, anti-allergy agents, analgesics, local anesthetics, antivirals, antibodies and molecules acting on the immune system, cytostatics and anticancer agents, hypolipidemics, vasodilators, vasoconstrictors, inhibitors of angiotensin-converting enzyme and phosphodiesterase, fenofibrate and derivatives thereof, statins, nitrate derivatives and anti-anginals, beta-blockers, calcium inhibitors, anti-diuretics and diuretics, bronchodilators, opiates and derivatives thereof, barbiturates, benzodiazepines, molecules acting on the central nervous system, nucleic acids, peptides, anthracenic compounds, paraffin oil, polyethylene glycol, mineral salts, antispasmodics, gastric anti-secretory agents, clay gastric dressings and polyvinylpyrrolidone, aluminum salts, calcium carbonates, magnesium carbonates, starch, derivatives of benzimidazole, and mixtures of the foregoing. Solid lipid nanoparticles in accordance with the present disclosure may also comprise a glucuronidation inhibitor, for example, piperine.

In certain embodiments, the solid lipid particles are devoid of active ingredient on their surface. Elimination of the active ingredient is obtained, for example, by washing the particles or by a suitable method. Thus, in a preferred embodiment, solid lipid particles in accordance with the present disclosure have no curcumin present at their surface. Thus, solid lipid particles in accordance with the present disclosure may not be coated.

Solid lipid particles in accordance with the present disclosure may be incorporated into any composition, including any cosmetic, pharmaceutical, veterinary, or food composition.

The present disclosure also relates to a composition containing at least one solid lipid particle as herein described. The composition may include any additive intended to modify its appearance or rheology. Additives that improve the fluidity of the solid lipid particles may also be included. For example, lubricants may be added, including, e.g., talc, starches, silica powders, anti-static agents, etc. In certain embodiments, the composition may be in the form of an aqueous suspension, syrup, or sachet. The composition may be in the form of any appropriate galenic formulation, such as capsules, gelatine capsules or gel capsules, granules, oral powders, dispersible powders, tablet, hydrodispersible and orodispersible tablets, etc. The composition may also be injectable. In this case, such compositions may include solid lipid particles having sizes ranging from about 0.5 µm to about 5 µm. Desired particle size distributions of solid lipid particles in accordance with the present disclosure may be obtained by sieving or equivalent sizing techniques.

Other embodiments of the present disclosure will be apparent to those skilled in the art from consideration of the specification and practice of the disclosed embodiments. The following examples should be considered as exemplary only, with a true scope and spirit of the present disclosure being indicated by the claims.

EXAMPLE 1

Preparation of Lipid Phase

The following materials were melted in a jacketed vessel held at temperature ranging from about 45° C. to about 75° C. (e.g. about 60° C.): a mixture of mono-, di-, and triglycerides having carbon number from $C_{10}$ to $C_{18}$ (commercially available as GELUCIRE® 43/10); glycerol dibehenate (commercially available as COMPRITOL® E); and lecithin (soy, sunflower).

Curcumin was added at a loading of about 15 weight percent and mixed into the vessel with an agitator (RPM ranging from about 200 RPM to about 600 RPM, e.g. 400 RPM). The resulting mixture of curcumin in lipid suspension was maintained at a temperature from about 45° C. to about 75° C. (e.g. 60° C.).

Preparation of Gel Phase

An appropriate amount of USP water or deionized water was weighed and transferred to a jacketed reactor equipped with an agitator. A polyacrylic polymer gelifying agent (commercially available under the trademark CARBOPOL®) was added. The concentration of the gelifying agent was from about 0.1 weight percent to about 0.8 weight percent (e.g., about 0.2 weight percent). The mixture was stirred at from about 200 RPM to about 800 RPM (e.g. about 400 RPM) until the dissolution of the gelifying agent was achieved. The pH of the gel was adjusted with 1N sodium hydroxide to a pH of about 3.5 to about 8.0 (e.g, about 4.5). The gel was then heated to about 60° C. under stirring/agitation.

Flash Injection

While stirring the gel (RPM ranging from about 200 RPM to about 800 RPM, e.g. 500 RPM), the lipid suspension obtained above was transferred via peristaltic pump directly into the gel held in the jacketed reactor. Agitation was terminated upon complete transfer. A dispersion was thus obtained.

Cooling and Separation

The temperature of the jacketed reactor was adjusted to a temperature of about 2° C. to about 10° C. (e.g. 5° C.). The temperature of the lipid phase of the dispersion was monitored to ascertain hardening. 1N sodium chloride solution was then added to the hardened lipid particles in the gel to break-up the gel. Agitation at about 100 RPM was used to aid gel break-up.

The contents of the jacketed reactor were then transferred to a Buchner funnel equipped with a membrane filter (50 µm to 100 µm pore size) and vacuum capability. Vacuum was applied until the solid lipid particles appeared dry and no more liquid was removed. The particles were washed with water and vacuum filtered again.

The filtered solid lipid particles were transferred to a drying tray and allowed to air dry. Alternatively, vacuum drying until the particles are free-flowing with no apparent moisture may be used. The solid lipid particles were then sieved to obtain a desired size distribution and collected.

EXAMPLE 2

The procedure of Example 1 was followed as above with the exception that instead of lecithin, propylene glycol caprylate (commercially available as CAPRYOL® 90) and medium-chain length triglycerides (carbon number ranging from $C_6$ to $C_{12}$, commercially available as LABRAFAC®) were used.

EXAMPLE 3

The procedure of Example 1 above was followed as above with the following exception. Prior to adding curcumin during preparation of the lipid phase, the curcumin was subjected to particle size reduction using a wet bead milling process for 30 minutes using a DYNO®-MILL to render the curcumin nanosized. The resulting curcumin particles had a particle size (average particle size diameter) ranging from about 0.1 µm to about 10 µm.

Figure 4:
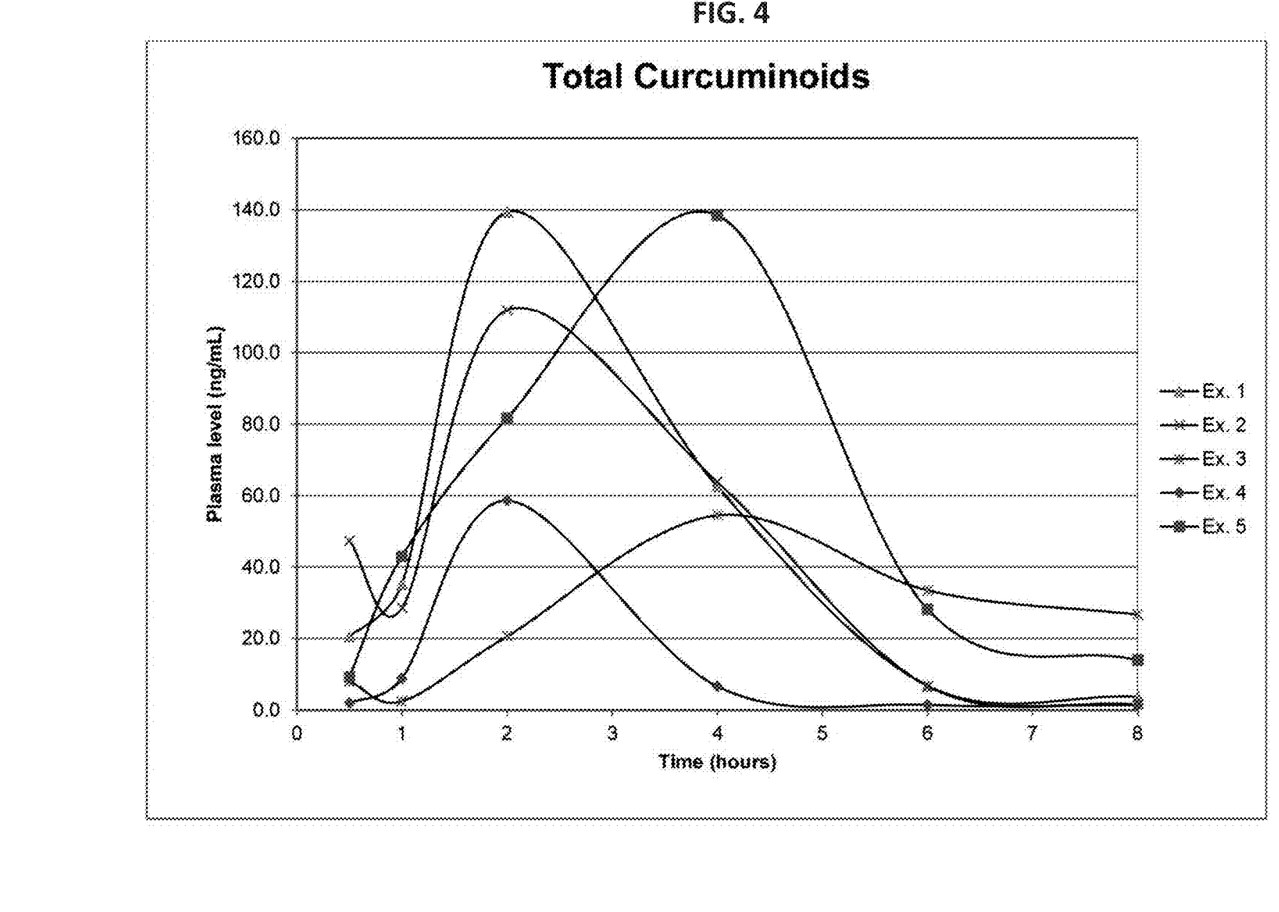
FIG. 4 is a graph of curcumin plasma concentration in dogs as a function of time following administration of Examples 1 to 5, described below.

The compositions of the Examples are summarized in Table 1, along with Examples 4 and 5, which do not employ solid lipid particles. Examples 1 to 5 were administered to fasted Beagle dogs weighing 10-12 kg. The curcumin equivalent dosage was 750 mg. Blood samples were taken at 0.5, 1, 2, 4, 6, and 8 hours following oral administration (oral gavage). Tests were run in triplicate. Curcumin concentration in the blood plasma was measured and recorded. A plot of the results (concentration of total curcuminoids over time) is shown in FIG. 4.

TABLE 1

| Example No. | Description | Composition | Dosage |
| --- | --- | --- | --- |
| 1 | SLP w/Lecithin | 15 wt. % Lecithin<br>15 wt. % Curcumin<br>5 wt. % COMPRITOL ® E<br>65 wt. % GELUCIRE ® 43/01 | 5 g |
| 2 | SLP w/propylene glycol caprylate, medium-chain triglycerides | 20 wt. % CAPRYOL ® 90<br>10 wt. % LABRAFAC ®<br>15 wt. % Curcumin<br>5 wt. % COMPRITOL ® E<br>50 wt. % GELUCIRE ® 43/01 | 5 g |
| 3 | SLP w/nanosized curcumin, propylene glycol caprylate, medium chain triglycerides | 20 wt. % CAPRYOL ® 90<br>10 wt. % LABRAFAC ®<br>15 wt. % Curcumin (nanosized; 0.1 µm to 10 µm)<br>5 wt. % COMPRITOL ® E<br>50 wt. % GELUCIRE ® 43/01 | 5 g |
| 4 | Neat curcumin | N/A | 750 mg |
| 5 | Commerical product MERIVA ® | Curcumin complex with phosophatidylcholine (formulation includes phosphate, maltodextrin, silica, magnesium stearate) | 5.3 g |

EXAMPLES 6, 7, AND 8

Solid lipid particles were made according to the Example 1. Example 6 was solid lipid particles comprising 80% Suppocire DM, 5% Compitrol E, and 15% curcumin. Example 7 was solid lipid particles comprising 70% Suppocire DM, 5% Compitrol E, 10% sunflower liquid lecithin, and 15% curcumin. Example 8 was solid lipid particles comprising 75% Suppocire DM, 5% Compitrol E, 6% sunflower powdered lecithin, and 15% curcumin.

The particles from Examples 6, 7, and 8 were dosed into a fasted animal model (Beagle dogs, 10-12 kg, three dogs per Example). Dogs were administered 750 mg curcumin in size 11 capsules. Tests were run in triplicate. Blood sampling was performed at 0.5, 1, 2, 4, 6, and 8 hours; plasma samples were treated with glucorodinase and sulfatase.

Table 2 shows the pharmacokinetic results (average, n=3). Examples 6, 7, and 8 gave good blood results with visually appealing, spherical solid lipid particles free of organic solvents.

TABLE 2

| Example | AUC (h*ng*ml) | $C_{max}$ (ng/ml) | $T_{max}$ (hr) |
| --- | --- | --- | --- |
| Example 6 | 49.4 | 14.9 | 4 |
| Example 7 | 136 | 40.7 | 2.3 |
| Example 8 | 131 | 39.2 | 2 |

What is claimed is:

1. Solid lipid particles comprising: a lipid hydrophobic matrix; and from about 5 wt. % to about 30 wt. % of curcumin, wherein said lipid hydrophobic matrix comprises
5 wt. % to 30 wt. % lecithin;
5 wt. % to 15 wt. % glycerol behenate; and
at least 40 wt. % mixture of monoglycerides, diglycerides, and triglycerides having a carbon number ranging from C6 to C40, and wherein said solid lipid particles have an average particle size diameter ranging from 100 µm to 1500 µm.

2. The solid lipid particles according to claim 1, wherein the lipid hydrophobic matrix has a melting point ranging from about 15° C. to about 85° C.

3. The solid lipid particles according to claim 1, wherein the lipid hydrophobic matrix has a melting point ranging from about 30° C. to about 45° C.

4. The solid lipid particles according to claim 1, wherein the curcumin has an average particle size diameter ranging from about 0.1 µm to about 10 µm.

5. The solid lipid particles according to claim 1, wherein the solid lipid particles have a substantially spherical shape.

6. A solid lipid particle according to claim 1, wherein the lipid hydrophobic mixture comprises
about 5 wt. % to about 15 wt. % curcumin
about 5 wt. % lecithin;
and at least 50 wt. % mixture of monoglycerides, diglycerides, and triglycerides having a carbon number ranging from $C_6$ to $C_{40}$.

7. The solid lipid particle of claim 1 comprising
about 15 wt. % curcumin
about 15 wt. % lecithin;
about 5 wt. % glycerol behenate; and
about 65 wt. % mixture of monoglycerides, diglycerides, and triglycerides having a carbon number ranging from $C_6$ to $C_{40}$.

8. The solid lipid particle of claim 1 comprising
15 wt. % curcumin
20 wt. % propylene glycol monocaprylate,
10 wt. % propylene glycol dicaprylate/dicaprate,
5 wt. % glycerol behenate, and
50 wt. % a mixture of monoglycerides, diglycerides, and triglycerides having a carbon number ranging from $C_6$ to $C_{40}$.

9. The solid lipid particle of claim 7 comprising:
15 wt. % curcumin wherein the curcumin has an average particle size diameter from about 0.1 µm to about 10 µm;
20 wt. % propylene glycol caprylate;
10 wt. % propylene glycol dicaprylate/dicaprate;
5 wt. % glycerol behenate, and 50 wt. % a mixture of monoglycerides, diglycerides, and triglycerides having a carbon number ranging from $C_6$ to $C_{40}$.

10. A solid lipid particle according to claim 1, wherein the curcumin is comprised in an amount of from 5% wt to 15% wt and wherein said solid lipid particle comprises:
   5% wt to 30% wt propylene glycol monocaprylate,
   5% wt to 30% wt propylene glycol dicaprylate/dicaprate,
   5% wt to 15% wt glycerol behenate,
   and at least 40% wt a mixture of monoglycerides, diglicerides, and triglicerides having a carbon number ranging from C6 to C40.

11. A pharmaceutical composition comprising one or more solid lipid particles according to claim 1.

12. A process for preparing solid lipid particles according to claim 1, wherein the process comprises:
   dispersing a lipid phase having a melting point ranging from about 15° C. to about 85° C. in a gel phase at a temperature above the melting point of the lipid phase to form a dispersion;
   cooling the dispersion to obtain solid lipid particles;
   separating the solid lipid particles; and
   optionally, washing the solid lipid particles;
   wherein the solid lipid particles comprise a lipid hydrophobic matrix; and from about 5 wt. % to about 30 wt. % of curcumin.

13. The process according to claim 12, wherein the solid lipid particle further comprise surfactant.

* * * * *

UNITED STATES PATENT AND TRADEMARK OFFICE
CERTIFICATE OF CORRECTION

PATENT NO. : 10,166,187 B2  
APPLICATION NO. : 15/786851  
DATED : January 1, 2019  
INVENTOR(S) : Diorio et al.

Page 1 of 1

It is certified that error appears in the above-identified patent and that said Letters Patent is hereby corrected as shown below:

In the Specification

Column 1, Line 19, "Curcum in" should read --Curcumin--.

Column 5, Lines 29-30, "oil may are mixed" should read --oil are mixed--.

Column 5, Line 47, "throughout such means" should read --throughout — such means--.

Signed and Sealed this  
Twenty-second Day of December, 2020

Andrei Iancu  
*Director of the United States Patent and Trademark Office*